US005876952A

United States Patent [19]
Shieh

[11] Patent Number: 5,876,952
[45] Date of Patent: Mar. 2, 1999

[54] NON-INVASIVE GLUCOSE BIOSENSOR: DETERMINATION OF GLUCOSE IN URINE

[76] Inventor: Paul Shieh, 43513 Greenhills Way, Fremont, Calif. 94539

[21] Appl. No.: 986,432

[22] Filed: Dec. 8, 1997

[51] Int. Cl.$^6$ .............................. C12Q 1/54; C12Q 1/00; C12Q 1/26; C12Q 1/28

[52] U.S. Cl. .................................. 435/14; 435/4; 435/25; 435/28; 435/817; 435/289.1; 435/283.1; 205/263; 205/571

[58] Field of Search .................................. 435/14, 4, 25, 435/28, 817, 289.1, 283.1; 205/263, 571

[56] References Cited

U.S. PATENT DOCUMENTS 5,645,710  7/1997  Shieh .......................................... 435/14
5,695,947  12/1997  Guo et al. .................................. 435/14

*Primary Examiner*—Louise N. Leary
*Attorney, Agent, or Firm*—Marvin S. Aronoff

[57] ABSTRACT

An amperometric glucose biosensor having high sensitivity and accuracy over a wide range of glucose concentrations and a method for the rapid detection of glucose in urine are provided. The biosensor strip comprises an electrically conductive carbon layer, having a first redox mediator, a reagent strip containing an enzyme system for the oxidation of glucose and a second redox mediator, and a silver/silver chloride reference electrode. In a preferred form of the sensor that has high sensitivity, a sensing electrode and a reference electrode are arranged so that the electrically conductive layers of the electrodes are face-to-face and sandwich the reagent strip between them. Screening for glucose is achieved by contacting the sensor with a drop of the patient's urine and comparing the current read-out with a standard calibration curve or by automatically converting the current flow generated by the test sample to units of glucose concentration. The sensor can measure urine glucose concentrations below 3 mg/dl. Measurement of urine glucose concentration with the sensor provides a non-invasive probe of a patient's blood glucose level since a linear relationship exists between blood glucose concentration and urine glucose concentration, approximately in the range between 0 to 400 mg/dl.

10 Claims, 3 Drawing Sheets

| URINE GLUCOSE CALIBRATION ||
| uA | GLUCOSE |
| --- | --- |
| 6 | 0 |
| 9 | 6.25 |
| 11 | 12.5 |
| 18 | 25 |
| 25 | 50 |
| 45 | 100 |
| 83 | 200 |

| BLOOD GLUCOSE AND URINE GLUCOSE RELATIONSHIP ||
|---|---|
| BLOOD GLU | URINE GLU |
| 87 | 0 |
| 95 | 2.5 |
| 96 | 3 |
| 114 | 12.5 |
| 130 | 12 |
| 132 | 12.5 |
| 171 | 55 |
| 200 | 77.5 |
| 215 | 125 |
| 217 | 130 |
| 239 | 185 |
| 269 | 244 |
| 385 | 345 |

| BLOOD GLUCOSE AND URINE GLUCOSE RELATIONSHIP ||
|---|---|
| BLOOD GLU | URINE GLU |
| 98 | 4 |
| 133 | 25 |
| 146 | 55 |
| 193 | 183 |
| 365 | 360 |

NON-INVASIVE GLUCOSE BIOSENSOR: DETERMINATION OF GLUCOSE IN URINE

CROSS REFERENCE TO RELATED APPLICATION

This application is related to the application entitled "A HIGHLY SENSITIVE AMPEROMETRIC BI-MEDIATOR-BASED GLUCOSE BIOSENSOR" BY DINGLI GUO, PAUL SHIEH AND ESFIR GOLDBERG, bearing the application Ser. No. 08/986,974, filed contemporaneously with the instant application, and hereby incorporated by reference.

BACKGROUND OF THE INVENTION

This invention deals with a method and means to accurately determine a wide range of glucose concentrations in urine, thereby providing a non-invasive glucose assay.

It has been well known in medicine that the existence of detectable levels of glucose in the urine may be indicative of diabetes. In effect, when there is too much glucose in the blood it spills over into the urine. Theoretically, glucose in the urine could reach an equilibrium with glucose in the blood. The accurate and reliable determination of glucose concentrations in urine would therefore provide a noninvasive procedure for the detection of diabetes and a means for monitoring the glycemic state of diabetes patients. Such a procedure would obviate the need to draw blood for analysis, which often must be done several times per day, on a routine basis, for certain types of diabetes patients. It would thus provide a painless and convenient approach to monitoring the glycemic state of an individual. In the case of diabetic patients whose blood glucose concentration must be monitored several times per day in order to manage diet and therapy, such a non-invasive procedure would provide the additional benefit of eliminating the danger of infection resulting from multiple skin punctures.

Currently, only one commercial product, Chemstrip uGK from Boehringer Mannheim Corporation, is available for urine glucose assay. This test is based on a colorimetric method and is not sensitive to low glucose concentrations. Urine glucose concentrations must be at least 40 mg/dl in order to produce a positive result. In practice, urine glucose concentrations must reach 100 mg/dl for formation of the green color on which the test is based. In order to obtain reliable positive results the patient's blood glucose must be 150 mg/dl or over in order to observe a positive result in this test.

There is a need for a highly sensitive, accurate and reliable device to determine glucose concentrations in urine, even at low concentrations, in order to conveniently and painlessly assay the glycemic state of both diabetic and normal patients. Such a device should be inexpensive, easy to manufacture and use and be capable of miniaturization.

BRIEF DESCRIPTION OF THE INVENTION

The present invention is directed to meeting the foregoing needs by providing a simple and convenient method of assaying urine glucose that utilizes an amperometric glucose biosensor having the sensitivity and linearity to assay glucose concentrations in the urine of normal as well as diabetic patients. Thus a painless, convenient, non-invasive method for screening patients for diabetes as well as determining the glycemic state of diabetic patients is provided.

The sensor of the present invention is an amperometric device that uses redox mediators and a bienzyme system to assay for glucose. It has high sensitivity and a wide range of linearity, thus enabling the direct and rapid measurement of glucose in biological fluids such as urine without sample concentration or dilution. Its high sensitivity enables glucose analyses to be run at potentials sufficiently low (e.g. −80 mV to −150 mV) to avoid erroneous results produced by interfering substances.

The amperometric glucose biosensor generally comprises a sensing electrode having a first redox mediator dispersed in an electrically conductive medium such as an electrically conductive graphite formulation; a reference electrode such as a standard silver—silver chloride (Ag/AgCl) or calomel electrode; a reagent strip containing a bienzyme system and reagents and a second redox mediator system in a gel medium.

The electrically conductive medium of the sensing electrode contains a first redox mediator comprising dimethylferrocene (DMF), ferricinium, ferrocene monocarboxylic acid (FCOOH), 7,7,8,8-tetracyanoquinodimethane (TCNQ), tetrathiafulvalene (TTF), nickelocene (Nc), N-methylacridinium ($NMA^+$), tetrathiatetracene (TTT), N-methylphenazinium ($NMP^+$), hydroquinone or mixtures thereof. The second redox mediator contained in the reagent strip may comprise a) various oxidizable compounds and mixtures such as 3-methyl-2-benzothiazolinone hydrazone hydrochloride and 3-dimethylaminobenzoic acid (MBTH-DMAB), 3-methyl-2-benzothiozolinone hydrazone and 2-methoxy-4-allyl phenol, 4-aminoantipyrine (AAP) and dimethylaniline, 4-aminoantipyrene and 4-methoxynaphthol, 3,3',5,5'-tetramethylbenzidine (TMB), 2,2-azino-di-[3-ethyl-benzthiazoline sulfonate], o-dianisidine, o-toluidine, sulfonated 2,4-dichloro-phenol and 4-amino phenazone, benzidine, or b) various redox compounds, ions and complexes such as $CN^-$, $Fe(CN)_6^{-4}$, $I^-$, $Co(NH_3)_6^{++}$, $Sn^{++}$, $S^{-2}$ or $Tl^{+2}$.

The reagent strip also contains a mixture of enzymes comprising glucose oxidase (GOX) and horseradish peroxidase (HRP); surfactants such as N-octanoyl-N-methyl-D-glucamine (MEGA 8), MEGA 10, Triton X-100, cholic acid, hydroxypropyl methylcellulose ("Methocel" 40-101 personal care grade), tetrapropylene diphenyloxide disulphonate sodium salt ("DOWFAX 2A1"), capryloamphocarboxypropionate ("MIRAROL J2M-SF"), polyoxyethylene 2 cetyl ether and mixtures thereof; stabilizers such as gelatin, bovine serum albumin, glutamate, L-arginine, Gantrez, mannitol, gum arabic polypep (low viscosity) and mixtures thereof; and a buffer to maintain pH between 4 and 8 such as citrate, succinate, tris-(hydroxymethyl) aminomethane, phosphate, 2(N-morpholino) ethanesulfonic acid and mixtures thereof.

The sensor may be constructed in many physical forms. In its most preferred form, which is highly sensitive, the sensing electrode and the reference electrode are formed as coatings on separate non-conductive strips such as polyester film, with these strips arranged so that they form "the bread" of a face-to-face sandwich in which the coated electrically conductive surfaces of the electrodes face each other and the reagent strip forms the "filling" of the sandwich. The general configuration of such a face-to-face sandwich with respect to the electrodes and the reagent strip is disclosed in Guo et al. U.S. patent application Ser. No. 08/471,026, now U.S. Pat. No. 5,695,947 which is herein incorporated by reference. In another form which is less sensitive, the sensing and reference electrodes, for example, may comprise strips, arranged in a side-by-side configuration with the reagent strip forming a bridge that connects them.

DESCRIPTION OF THE PREFERRED EMBODIMENTS

The sensor of the present invention is an amperometric device that uses redox mediators and a bienzyme system to assay for glucose. It has high sensitivity and a wide range of linearity, thus enabling the direct and rapid measurement of glucose even at low concentrations in biological fluids such as urine without sample concentration or dilution. Its high sensitivity enables glucose analyses to be run at potentials sufficiently low (e.g. −80 mV to −150 mV, with −125 mV preferred) to avoid erroneous results produced by interfering substances.

Figure 1A:
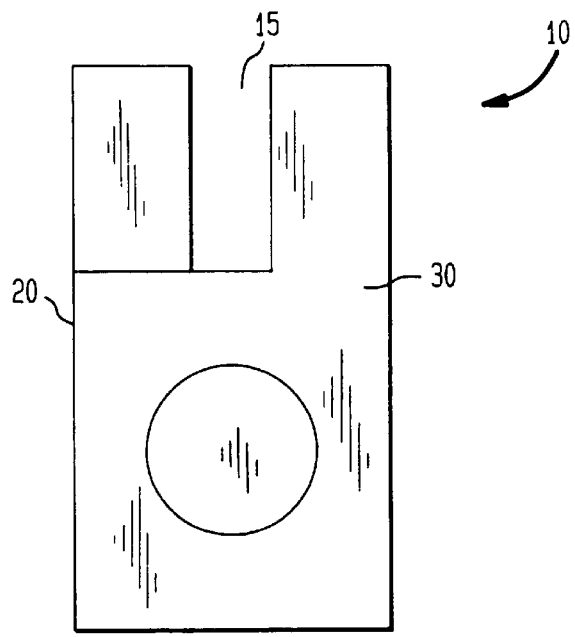
FIG. 1A is an overview of a high sensitivity amperometric glucose sensor having a face-to-face sandwich configuration.
Figure 1B:
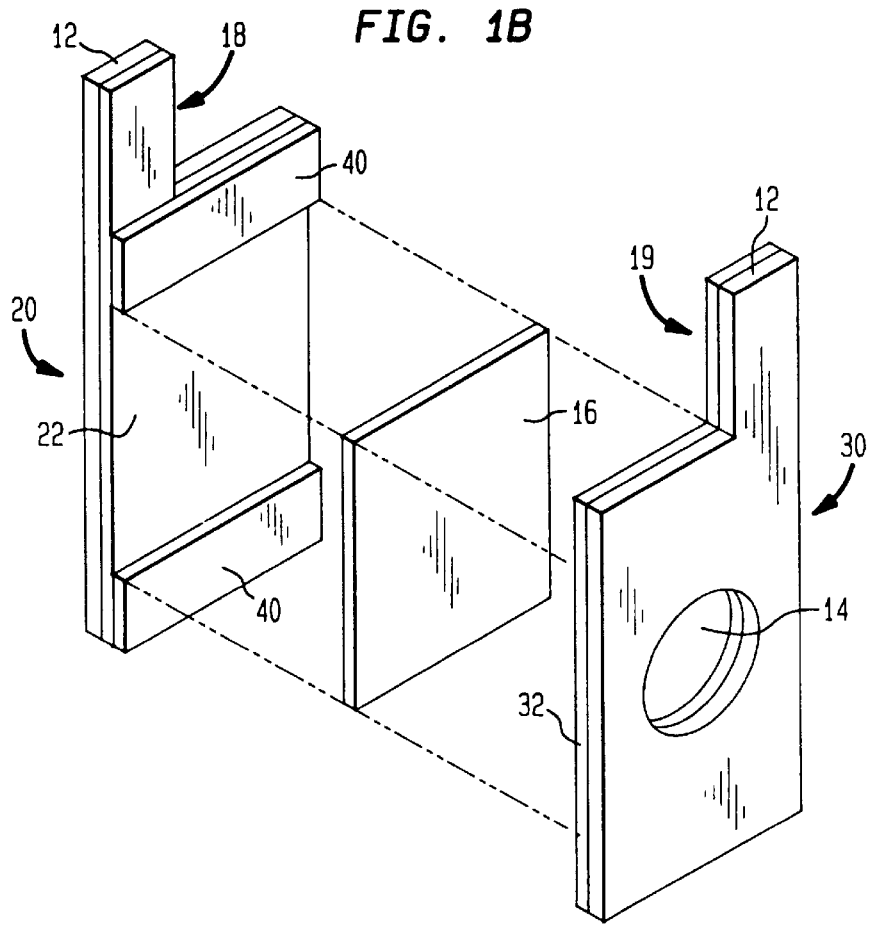
FIG. 1B is an exploded view of the glucose sensor of FIG. 1A.
Figure 1C:
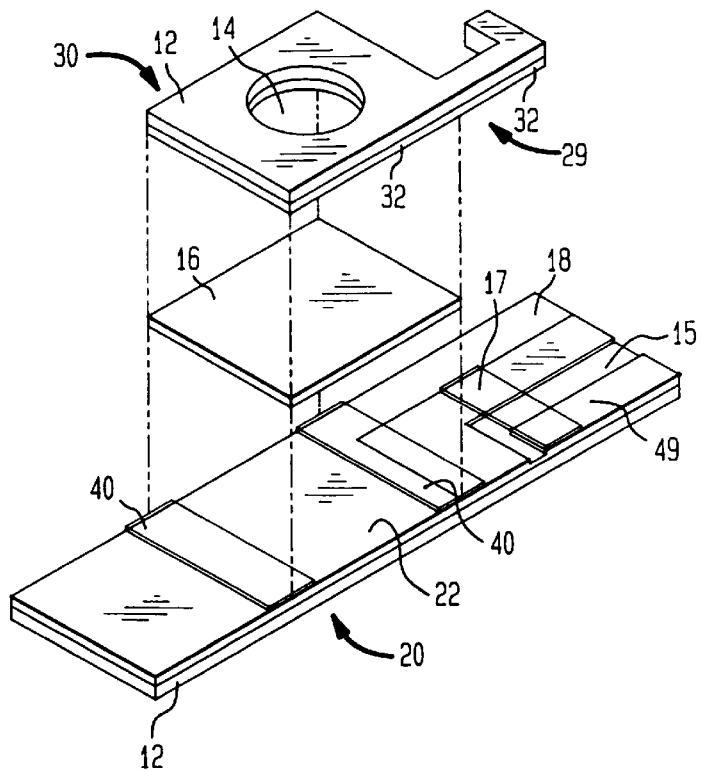
FIG. 1C is an exploded view of a variation of the glucose sensor of FIG. 1A.

A version of the glucose sensor of the present invention that is preferred due to its high sensitivity is shown in FIGS. 1A and 1B. FIG. 1A, is an overview or top view and FIG. 1B is an exploded view of the biosensor of FIG. 1A. The glucose sensor 10 generally comprises a sensing electrode 20, a reference electrode 30 and reagent strip 16. In the version of the sensor depicted in FIGS. 1A–1B, the sensing electrode 20 has a conductive protrusion 18 and reference electrode 30 and has a conductive protrusion 19 separated by gap 15. Protrusions 18 and 19 serve as convenient points for rapid electrical connection. FIG. 1C is an exploded view of a variation of the glucose sensor depicted in FIGS. 1A–1B in which conductive protrusion 19 of the reference electrode is replaced with conductive arm 29, which is coated with the electrically conductive formulation of the reference electrode. The electrically conductive surface of conductive arm 29 makes contact with electrically conductive face-up protrusion 49, via electrically conductive connecting means 17. Electrically conductive protrusion 49 on sensing electrode 20 is typically a carbon strip. The electrically conductive connecting means 17 holding arm 29 in contact with face-up protrusion 49 is typically an electrically conducting adhesive transfer tape such as 3M Scotch 9703. In the variation of FIG. 1C, the electrically conductive surfaces of protrusions 18 and 49 are both face up, thereby facilitating electrical connection with some types of connectors.

Reagent strip 16 is sandwiched between sensing electrode 20 and reference electrode 30. Opening 14 in reference electrode 30 is provided for introduction of a liquid sample. The sandwich configuration may be optionally held together by clamps, tape and the like. Optionally, spacers 40 may be used to keep sensing electrode 20 and reference electrode 30 physically separated. Spacers 40 may comprise any non-conductive adhesive means, such as adhesives and double sided adhesive tape.

Sensing electrode 20 comprises a non-conductive support member 12 for electrically conductive layer 22. The non-conductive support member may typically be any cohesive non-conductor such as any non-conductive film or sheet forming polymeric material, ceramics, glass, paper, cardboard. The preferred thickness of the non-conductive support material is from about 5 mil to about 10 mil. Polymeric materials, particularly non-conductive polymerics in the form of films or thin sheets are preferred as they may be readily cut to strips of suitable size. In practice non-conductive support 12 is a polymeric film or sheet. Any non-conductive polymeric film or sheet such as polyvinylchloride, polyester, polycarbonate, vinyl acetate copolymer, nylon, poly (1,4-butyleneterephthalate), cellulose propionate, ethylene/acrylic acid copolymer, polybutadiene, polyethylene, polypropylene, polyimide, acrylic film, polyurethane, polystyrene, and polyvinylfluoride may be used. Polyester film such as Mylar is preferred as it is readily available and easily handled.

Electrically conductive layer 22 of sensing electrode 20 comprises an electrically conductive layer containing a redox mediator. Electrically conductive layer 22 may be formed from any metallic or non-metallic conductor having a physical state that can be blended with one or more redox mediators and deposited on non-conductive support layer 12 to form an electrically conductive layer. The electrically conductive layer may comprise electrically conductive carbon or graphite, copper, silver, gold, platinum, nickel, stainless steel, iron and other conductive materials and mixtures thereof. Formulations of electrically conductive graphite or carbon and polymeric substances are preferred. Formulations of electrically conductive carbon or graphite containing polymeric material such as the electrically conductive inks (e.g. ERCON G-448(I) or G-449(I)) available from Ercon Inc.(Waltham, Mass.) are most preferred as they are readily available, can be uniformly spread on a non-conductive support member 12 to form a thin layer and can be easily blended with a redox mediator. Redox mediators which may be blended with electrically conductive formulations based on electrically conductive inks include dimethyl ferrocene (DMF), ferricinium, ferrocenecarboxylic acid, 7,7,8,8-tetracyanoquinodimethane (TCNQ), tetrathiafulvalene (TTF), hydroquinone, Nicklocene (Nc), N-methylacridinium (NMA), Tetrathiatetracene (TTT), N-methylphenazinium (NMP+), and mixtures thereof. DMF is preferred as it gives an easily detectable current change with change of glucose concentration when used in conjunction with a second redox mediator in the reagent strip 16. The preferred concentration of the redox mediator in the electrically conductive layer 22, based on the total weight of the dry electrically conductive layer 22, ranges from about 0.2% to about 15% with a concentration of about 1% to about 9% most preferred. Example 1a illustrates one process for making an embodiment of sensing electrode 20. Other processes known in the art, for example, stencil printing may also be used to make sensing electrode 20.

The term redox mediator is herein defined as a substance or substances that facilitates the flow of electrons in a reduction—oxidation reaction, so that the reaction may occur at a lower potential than when such substance or substances are absent.

Reference electrode 30 comprises a non-conductive support member 12 for electrically conductive layer 32. The non-conductive support member may typically be any cohesive non-conductor such as any non-conductive film or sheet forming polymeric material, ceramics, glass, paper, cardboard. The preferred thickness of the non-conductive support material is from about 5 mil to about 10 mil. Polymeric materials, particularly non-electrically conductive polymerics in the form of films or sheets are preferred as they may be readily cut to strips of suitable size. In practice, non-conductive support 12 is a polymeric film or sheet. Any non-conductive polymeric film or sheet such as those used for the sensing electrode may be used. Polyester film such as Mylar is preferred as it is readily available and easily handled.

Electrically conductive layer 32 of reference electrode 30 comprises a Ag/AgCl reference electrode prepared by coating a base support such as polyester film or PVC film with an electrically conductive formulation comprising Ag/Cl dispersed in a resin formulation, such as ERCON R-421 (DBE-60) Ag/AgCl and curing the coating for about one hour at about 70° C. Other forms of reference electrodes may be used such as the Ag/AgCl reference electrodes described in U.S. Pat. No. 5,401,377, which is herein incorporated by reference to the extent that it is pertinent, however, Ag/AgCl electrodes based on Ag/AgCl electrically conductive formulations which may be conveniently spread on a non-conductive base are preferred. Other types of reference electrodes such as the standard calomel electrode may also be used providing that they have an active surface that can be brought into electrical contact with the reagent strip of the sensor. Example 1b illustrates one process for making an embodiment of reference electrode 30. Other processes known in the art, for example, stencil printing may also be used to make reference electrode 30.

Reagent Strip

Reagent strip 16 comprises a porous or fibrous water absorbent carrier impregnated with a reagent formulation. The carrier may be any water absorbent, porous medium including film, non-woven fabrics, felts, cellulosic papers, non-cellulosic papers, papers based on mixtures of cellulosic and non-cellulosic fibers or any water absorbent fibrous matrix, but commercially available cellulosic non-cellulosic papers such as Baxter S/P qualitative filter paper grade 360, Brawny paper (2-ply paper towel produced by James River Corp., Norwalk, Conn.), Leukosorb A and B polyester paper, Loprosorb and Loprodyne Nylon 66, Biodyne A amphoteric Nylon 66 membrane (Pall Corp., Glen Cove, N.Y.), Whatman filter paper Number 1, 3, 4 and 114, Teri-plus 4-ply and KimTowel (Kimberly-Clark, Roswell, Ga.) are preferred as they have an adequate degree of absorbency for the reagent formulation.

The reagent formulation contained in reagent strip 16 comprises a second compound or mixture of compounds that can function as a second redox mediator in addition to the first redox mediator which is contained in the sensing electrode, surfactants, and stabilizers. Compounds and mixtures of compounds that can function as the second redox mediator are compounds that can be oxidized by hydrogen peroxide under catalysis by horseradish peroxide (HRP). Such compounds may comprise various substances such as a) various oxidizable compounds and mixtures such as 3-methyl-2-benzothiazolinone hydrazone hydrochloride and 3-dimethylaminobenzoic acid (MBTH-DMAB), 3-methyl-2-benzothiozolinone hydrazone and 2-methoxy-4-allyl phenol, 4-aminoantipyrine (AAP) and dimethylaniline, 4-aminoantipyrene and 4-methoxynaphthol, 3,3',5,5'-tetramethylbenzidine (TMB), 2,2-azino-di-[3-ethylbenzthiazoline sulfonate], o-dianisidine, o-toluidine, sulfonated 2,4-dichloro-phenol and 4-amino phenazone, benzidine, or b) various redox compounds, ions and complexes such as $CN^-$, $Fe(CN)_6^{-4}$, $I^-$, $Co(NH_3)_6^{++}$, $Sn^{++}$, $S^{-2}$ or $Tl^{+2}$. Ferrocyanide ($Fe(CN)_6^{-4}$) is preferred as it generally produces relatively large changes in current flow with changes of glucose concentration over a wide range. The weight of the second redox mediator in reagent strip 16 ranges from about 0.001 mg to about 1 mg per sensor reagent strip with the preferred weight range from about 0.1 mg to about 0.6 mg for a sensor having a reagent strip surface area of about 70 mm².

The reagent formulation contained in reagent strip 16 further comprises glucose oxidase (GOX) and horseradish peroxidase (HRP). The concentration of GOX in the reagent strip ranges from about 5 IU to about 80 IU with a concentration of about 35 IU to about 50 IU preferred. The concentration of HRP in the reagent strip ranges from about 0.5 IU to about 10 IU with a concentration of about 4 IU to about 6 IU preferred.

An illustrative scheme of the chemical reactions of the bi-mediator, bi-enzyme system in which the first mediator contained in the sensing electrode is DMF and the second mediator contained in the reagent strip is ferrocyanide is as follows:

1. $C_6H_{12}O_6$ (glucose)$+O_2$—GOX—>$C_6H_{10}O_6$ (gluconic acid)$+H_2O_2$
2. $H_2O_2+2\ [Fe(CN)_6]^{-4}+2H^+$—HRP—>$2H_2O+2[Fe(CN)_6]^{-3}$
3. $[Fe(CN)_6]^{-3}+DMF$ (reduced)→$[Fe(CN)_6]^{-4}+DMF$ (oxidized)
4. DMF (oxidized)$+e^-$(from electrode)→DMF (reduced)

The reagent strip formulation further comprises a buffering agent to maintain the pH between about 4 and about 8. Any buffering agent may be used that can maintain the pH in this range providing it does not interfere with the electron transfer reactions of the biosensor. For example, buffers such as citrate, succinate, tris-(hydroxymethyl) aminomethane, phosphate, 2(N-morpholino) ethanesulfonic acid and mixtures thereof may be used. Citrate buffer is preferred to maintain the pH in the preferred range of about 4.5 to about 5.5. The preferred concentration of buffer ranges from about 0.00625 mole to about 0.05 mole per sensor reagent strip, with the most preferred concentration ranging from about 0.0125 mole to about 0.025 mole per sensor.

The surfactants used in reagent strip 16 comprise N-octanoyl-N-methyl-D-glucamine (MEGA 8), N-decanoyl-N-methyl-D-glucamine (MEGA 10), Triton X-100, cholic acid, hydroxypropyl methylcellulose ("Methocel" 40-101 personal care grade), tetrapropylene diphenyloxide disulphonate sodium salt ("DOWFAX 2A1"), capryloamphocarboxypropionate ("MIRAROL J2M-SF"), polyoxyethylene 2 cetyl ether, polyethylene glycol, sodium lauryl sulfate, sodium lauryl sarcosinate, Surfynol 485 (2,4, 7,9-tetramethyl-5-decyne-4,7-diol ethoxylate(30)), and mixtures thereof used either separately or in combination. A preferred surfactant is MEGA 8. More preferred is a mixture of Surfynol 485 and MEGA-8. The preferred weight of surfactant ranges from about 0.1 mg to about 100 mg per sensor, with the most preferred weight ranging from about 5 mg to about 12 mg per sensor.

Any water soluble or water dispersible aqueous thickening or gelling agent may be used as a stabilizer in reagent strip 16 providing it does not interfere with chemical processes which occur during the glucose assay. Preferred stabilizers include gelatin, bovine serum albumin, glutamate, L-arginine, Gantrez, mannitol, gum arabic, polypep (low viscosity), methocel and mixtures thereof used separately or in combination. The weight of any stabilizer may range from about 0.00005 mg to about 100 mg per sensor, with the preferred range being about 1 mg to about 5 mg per sensor.

Example 1C illustrates a process for making an embodiment of reagent strip 16. Generally, when the reagent strip is wet, as by contact with water or a liquid sample, electrical contact is made between the sensing electrode and reference electrode in most embodiments of the sensor.

The embodiments of the invention and their use are further illustrated by way of the following examples.

EXAMPLE 1A

This example illustrates the construction of a sensing electrode of the present invention. An equal amount by weight of graphite ink (Ercon G-448(I) Graphite, Ercon Inc) and electrically conductive graphite powder (Fisher Scientific.Co, Pittsburg, Pa.) were mixed. This mixture was mixed with 10% DMF in toluene/alcohol(1/1) or DBE solvent to attain a mixture with a dynamic viscosity of about $2 \times 10^4$ poise at frequency of 1 radius/second. This mixture was laid down on a Mylar or PVC film base support and spread with a steel doctor knife having a gap of about 0.5 to about 6 mil to produce an evenly distributed thin layer. The graphite coating was cured at about 40° C. for 90 minutes. The electrode may also be fabricated by other methods known in the art such as stencil coating. Normally an approximately 5 mil stencil can be used.

EXAMPLE 1B

This example illustrates the general procedure for preparation of a reference electrode. A commercial polymer base Ag/AgCl ink (e.g. from Ercon, Inc.) was laid down on a Mylar base support and spread with a steel doctor knife with a gap ranging from 0.5 mil to 6 mil to obtain an evenly distributed thin layer. Typically the thickness of the wet material was about 1 mil. The Ag/AgCl coating was cured in an oven at 70° C. for one hour. The electrode may also be fabricated by other methods known in the art such as stencil coating.

EXAMPLE 1C

A version of the reagent strip for the glucose sensor was prepared as follows:

The paper or film comprising the water absorbent reagent strip is impregnated with an aqueous enzyme system and redox compound formulation having 800 units per ml GOX, 80 units per ml HRP, 1% potassium ferrocyanide, 0.5% Mega 8, 0.0005% gelatin, and about 0.2M sodium citrate to adjust the pH to 5. Two pieces of approximately 4×8 cm Brawny paper were immersed in this solution for about 20 seconds and then transferred to a nylon net and dried in an oven at 40° C. for 20 minutes. This procedure was repeated once on the previously impregnated paper. The paper was then redried in an oven at 40° C. to constant weight.

EXAMPLE 1D

This example illustrates one method for the construction of a version of the glucose sensor having a face-to-face sandwich configuration using the elements prepared in Examples 1 a, b and c. This version of the face-to-face configuration is shown in FIG. 1A and FIG. 1B. A hole was punched out through a section of the reference electrode. Double sided adhesive tape (e.g. 3M #415 and 465; and ARcare® #7148, 7840 and 7841 (Adhesives Research Inc., Glen Rock, Pa.) was applied to the active surface (i.e. electrically conductive layer) of the reference electrode on both sides of the punched out hole. A piece of reagent strip prepared as in Example 1c was placed over the punched out hole between the two pieces of double sided tape. The sensing electrode was then placed over the reference electrode so that its active surface (i.e. electrically conductive layer) made contact with the reagent strip and pressed down, so that it adhered to the double faced tape, forming a sandwich, in which the active surfaces faced each other and the reagent strip was sandwiched between the active surfaces and was in contact with them. A similar procedure is used to construct a variation of the face-to-face sensor depicted in FIG. 1C. In this case, however, a piece of electrically conducting adhesive transfer tape such as 3M Scotch 9703 was used to make electrical contact between arm 29 and face-up protrusion 49.

EXAMPLE 2

This example illustrates the linear correlation of glucose concentration with current flow and the establishment of a calibration curve for glucose concentration using the sensor constructed in Examples 1A–1D.

Figure 2:
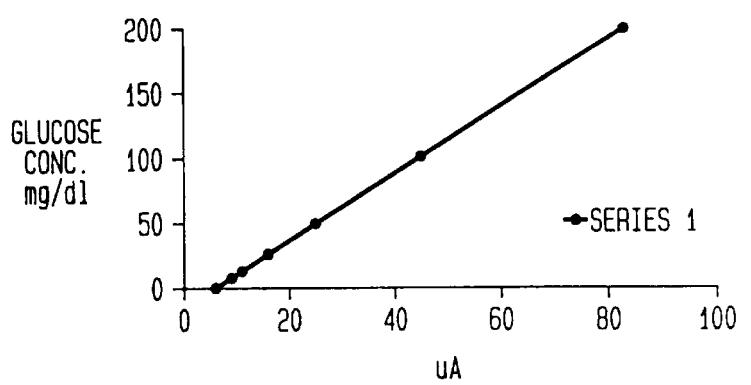
FIG. 2 is a calibration curve of the glucose sensors for the determination of glucose in urine.

The response of the glucose samples was measured amperometrically under an applied constant potential of −125 mV from a constant power source. The response was recorded at regular intervals either manually or electronically by a data acquisition system via an IEEE 488 computer interface. Timing was initiated with the addition of a measured sample (about 15 $\mu$l) to the reagent strip. The current generated from the enzymatic redox reactions was detected by a picoammeter or an electrometer. Glucose concentrations of 6.25, 12.5, 25, 50, 100 and 200 mg/dl were measured within 30 seconds using commercially available synthetic human serum standards from Verichemi Lab Inc., Providence, R.I. The linear response obtained is depicted in FIG. 2. After calibration in this way, glucose concentration of unknown samples may be directly read on a meter.

EXAMPLE 3

This example illustrates the ability of the sensor to quantitatively detect normal and abnormal human urine glucose concentrations.

The procedure of Example 2 was applied to urine specimens obtained from non-diabetic and from diabetic patients. Urine glucose concentrations were determined using the calibration curve of FIG. 2.

For the non-diabetic patients all urine glucose concentrations were under 5 mg/dl. This corresponded to a blood glucose level of 90 mg/dl or less as determined by a commercial blood glucose tester (Lifescan One Touch Glucometer). In the case of a patient having a normal base urine glucose level of 5 mg/dl an increase in urine glucose level to 7 mg/dl was detected using the procedure of Example 2 within 30 minutes after eating a doughnut. This corresponded to a blood glucose level of 105 mg/dl as determined with the Lifescan One Touch Glucometer.

The fasting urine glucose level of a diabetes patient, whose diabetes was under control, was found to be 25 mg/dl using the procedure of Example 2, while the patient's blood glucose level was 133 mg/dl as determined by the Lifescan One Touch Glucometer. An increase in urine glucose level to 360 mg/dl was detected using the procedure of Example 2 within 30 minutes after the patient ate a sweet roll. The corresponding blood glucose level was 366 mg/dl as determined with the Lifescan One Touch Glucometer. Glucose levels were remeasured within 2 hours after the patient resumed taking their normal diabetes medication. Using the procedure of Example 2 urine glucose level was found to be under 33 mg/dl with a corresponding blood glucose level of 146 mg/dl as determined with the Lifescan One Touch Glucometer.

By testing the urine of presenting patients whose glycemic state is unknown, the sensor of the present invention can be used as a quantitative screen for diabetes. It can also serve as a means to monitor the immediate glycemic state of a diabetic and to determine the immediate effectiveness of treatment in reducing blood glucose level as reflected in urine glucose level without the need to draw blood.

EXAMPLE 4

This example depicts the performance of the glucose sensor of the present invention in determining urine glucose levels and blood glucose levels and shows that a linear relationship exists between these levels. Urine glucose concentrations were determined using the calibration curve of FIG. 2.

Figure 3:
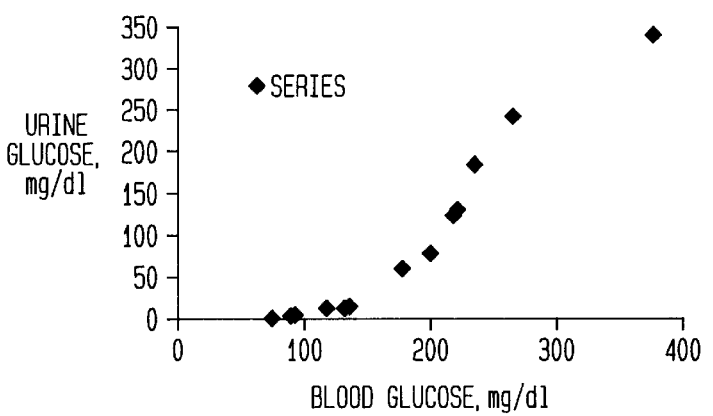
FIG. 3 is a graphical representation of the relationship between blood glucose concentration and urine glucose concentration.
Figure 4:
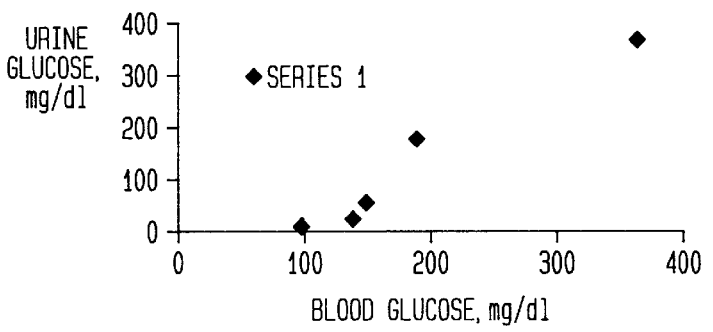
FIG. 4 is another graphical representation of the relationship between blood glucose concentration and urine glucose concentration.

Urine samples were obtained from individuals that had fasted for various periods of time and urine glucose concentration was correlated with the concentration of glucose in a blood sample taken at the same time using the Lifescan One Touch Glucometer. Two series of such tests were conducted over a period of about one year. These results are depicted in FIG. 3 and FIG. 4. It can be seen that once the blood glucose level exceeds about 90 mg/dl there is "spill over" into the urine where it can be quantitatively detected using the amperometric glucose sensor disclosed herein and the calibration curve developed in Example 2. As can be seen in FIGS. 3 and 4 urine glucose level approaches blood glucose level at the higher blood glucose levels that might be found in an individual having uncontrolled diabetes. Thus the procedure and amperometric sensor disclosed herein can be conveniently used to non-invasively screen for diabetes as well as monitor the glycemic state of a diabetic.

In the course of correlating blood glucose levels with urine glucose levels using the sensor and method of the instant disclosure, it was occasionally found that diabetic patients having blood glucose levels of about 150 mg/dl had urine glucose levels far above the range to be expected from FIGS. 3 and 4. Such mismatches can be attributed to other pathologies associated with the release of large quantities of glucose to the urine such as kidney or liver disease. Thus the method of precisely correlating blood glucose level with urine glucose level of the present disclosure can also be applied to screening for kidney and liver diseases characterized by releasing high quantities of glucose to the urine while the blood glucose level remains relatively low or only moderately elevated.

As indicated in FIGS. 3 and 4 there is a linear relationship between blood glucose concentration and urine glucose concentration approximately in the range between 0 to 400 mg/dl. Therefore, by a providing a highly accurate, precise and sensitive means to measure urine glucose concentration, the biosensor and method of the present invention can be used as a non-invasive probe of a patient's blood glucose level. By this means patients, particularly diabetic patients, who must regularly provide a blood sample via pin-prick or syringe, can avoid the pain and inconvenience of blood sampling and still obtain an accurate picture of their glycemic state. Diabetic patients could monitor their glycemic state many times per day and in almost any place. The biosensor and test method of the present invention have the further advantage of providing results rapidly, that is, within 30 seconds, and permit the use of a direct readout as on LCD readout devices, thus obviating the need for color chart comparison. The high sensitivity of the amperometric glucose sensor of the present invention permits detection of urine glucose levels as low as 3 mg/dl, which is considerably lower than the detection limit of optical types of urine glucose sensors. Yet another advantage of the sensor of the present invention is its disposability. It is also easy to manufacture by methods known in the art such as screen printing and is cost effective.

The sensor of the present invention may comprise part of a kit including electronic means to automatically calculate and or chart a patient's current glycemic state. Although the present invention has been described in considerable detail with reference to certain preferred versions thereof, other versions are possible. For example, other versions of the glucose biosensor are possible as is its use in conjunction with instrumentation such as devices for automatically assaying large numbers of samples. Versions of the glucose biosensor of the present invention may also comprise a portion of an analytical kit. The glucose biosensor of the present invention may also be used to assay a wide variety of glucose containing fluids of biological, agricultural and industrial origin. Therefore, the spirit and scope of the appended claims should not be limited to the description of the preferred versions contained herein.

What is claimed is:

1. A non-invasive method which measures the glucose concentration of a sample for determining the glycemic state of a patient which measures the glucose concentration of a sample comprising the steps a) providing an amperometric biosensor for glucose comprising;

a sensing electrode, the sensing electrode comprising;

a non-conductive support member, with the non-conductive support member comprising;

a non-conductive polymeric film;

the non-conductive polymeric film coated with an electrically conductive layer, and the electrically conductive layer comprising;

an electrically conductive carbon or graphite formulation containing a first redox mediator, with the first redox mediator selected from the group consisting of;

dimethylferrocene, ferricinium, ferrocene monocarboxylic acid, 7,7,8,8-tetracyanoquinodimethane, tetrathiafulvalene, nickelocene, N-methylacridinium, tetrathiatetracene, N-methylphenazinium, hydroquinone and mixtures thereof, and a reference electrode comprising;

a non-conductive polymeric film, the polymeric film coated with an electrically conductive formulation comprising Ag/AgCl dispersed in a resin formulation, and with the reference electrode having an opening; and a reagent strip, the reagent strip comprising;

a carrier strip that is a porous or fibrous water absorbent matrix, the carrier strip impregnated with a mixture comprising;

glucose oxidase,
        horseradish peroxidase
        a second redox mediator, the second redox mediator selected from the group consisting of;

3,3'5,5'-tetramethylbenzidine, 3-methyl-2-benzothiazolinone hydrazone hydrochloride and 3-dimethylaminobenzoic acid, o-dianisidine, o-toluidine, sulfonated 2,4-dichloro-phenol and 4-amino phenazone benzidine, 3-methyl-2-benzothiozolinone hydrazone and 3-(dimethylamino) benzoic acid, 3-methyl-2-benzothiozolinone hydrazone and 2-methoxy-4-allyl phenol, 4-aminoantipyrene-dimethylaniline and 4-aminoantipyrene-4-methoxynaphthol, (Fe(CN)$_6$$^{-4}$), HCN, I$^-$, Co(NH$_3$)$_6$$^{+2}$, Sn$^{+2}$, S$^{-2}$, Tl$^{+2}$ and mixtures thereof, at least one surfactant, the surfactant selected from the group consisting of;
  cholic acid, Triton X-100, polyethylene glycol, sodium lauryl sulfate, sodium lauryl sarcosinate, hydroxypropyl methylcellulose, tetrapropylene diphenyloxide disulphonate sodium salt, capryloamphocarboxypropionate, polyoxyethylene-2-cetyl ether, 2,4,7,9-tetramethyl-5-decyne-4,7-diol ethoxylate, octanoyl-N-methyl-D-glucamide, decanoyl-N-methyl-D-glucamide and mixtures thereof,
at least one stabilizer, the stabilizer selected from the group consisting of;
  gelatin, bovine serum albumin, glutamate, L-arginine, Gantrez, mannitol, gum arabic, low viscosity polypep, methocel and mixtures thereof,
a buffering agent to maintain a pH from about 4 to about 8, the buffering agent selected from the group consisting of;
  citrate, succinate, tris-(hydroxymethyl) aminomethane, phosphate, 2(N-morpholino) ethanesulfonic acid and mixtures thereof,
with the electrically conducting layer of the sensing electrode and the electrically conductive formulation of the reference electrode facing each other; and with the reagent strip superimposed on and in physical contact with the electrically conducting layer of the sensing electrode, and with the reference electrode superimposed on the reagent strip so that the electrically conductive formulation coating the reference electrode is superimposed on the reagent strip and in physical contact with the reagent strip; so that the sensing electrode and the reagent strip and the reference electrode form a sandwich;

b) maintaining a potential of about −80 mV to about −125 mV across the sensing electrode and the reference electrode;

c) introducing a non-invasively obtained biological fluid sample into the opening of the reference electrode;

d) measuring the current passing between the sensing electrode and the reference electrode;

e) comparing the current measured to a calibration curve of the concentration of glucose versus current at the potential used in step c) to obtain the concentration of glucose in the non-invasively obtained biological fluid sample.

2. The method of claim 1 further comprising the step of: comparing the concentration of glucose in the non-invasively obtained biological fluid sample to a correlation of blood glucose concentration with non-invasively obtained biological fluid glucose concentration to obtain the concentration of glucose in the blood.

3. The method of claim 1 in which the polymeric film comprising the non-conductive support member of the sensing electrode and the non-conductive support member of the reference electrode of step a) comprises polyester and the first redox mediator comprising the electrically conducting layer of step a) is 1,1' dimethylferrocene and the second redox mediator comprising the reagent strip of step a) is selected from the group consisting of 3,3',5,5' tetramethylbenzidine, potassium ferrocyanide and mixtures thereof.

4. The method of claim 3 in which the surfactant comprising the reagent strip of step a) is selected from the group consisting of 2,4,7,9-tetramethyl-5-decyne-4,7-diol ethoxylate, octanoyl-N-methyl-D-glucamide and mixtures thereof.

5. The method of claim 4 in which the buffering agent comprising the reagent strip of step a) is a citrate salt.

6. The method of claim 5 further comprising the step of:
  comparing the concentration of glucose in the non-invasively obtained biological fluid sample to a correlation of blood glucose concentration with non-invasively obtained biological fluid glucose concentration to obtain the concentration of glucose in the blood.

7. The method of claim 1 in which the reference electrode of step a) further comprises a protrusion having an electrically conductive coating with the coating electrically connected to the coating of the reference electrode and coplanar with the coating of the reference electrode; and the sensing electrode of step a) further comprises a protrusion having a first conductive zone and a second conductive zone, with the first and the second conductive zones coplanar with the electrically conductive coating of the sensing electrode and with the first conductive zone electrically connected to the sensing electrode and with the second conductive zone not electrically connected to the sensing electrode; and with the electrically conductive coating of the reference electrode protrusion superimposed on the second conductive zone on the sensing electrode protrusion and brought into electrical contact with the second conductive zone on the protrusion of the sensing electrode at a contact zone by means of an electrically conductive connector; and with the second conductive zone on the sensing electrode extending beyond the contact zone.

8. The method of claim 1 in which the non-invasively obtained biological fluid is urine.

9. The method of claim 2 in which the non-invasively obtained biological fluid is urine.

10. The method of claim 5 in which the non-invasively obtained biological fluid is urine.

* * * * *

UNITED STATES PATENT AND TRADEMARK OFFICE
CERTIFICATE OF CORRECTION

PATENT NO. : 5,876,952
DATED : March 2, 1999
INVENTOR(S) : Paul Shieh

It is certified that error appears in the above-identified patent and that said Letters Patent is hereby corrected as shown below:

In claim 1, column 10, line 18 after "method" delete the phrase "which measures the glucose concentration of a sample".

In claim 1, column 10, line 21 after "steps" insert --of:--.

Signed and Sealed this

Twenty-first Day of September, 1999

Attest:

Q. TODD DICKINSON

*Attesting Officer*        *Acting Commissioner of Patents and Trademarks*